United States Patent [19]
Pietrzak et al.

[11] Patent Number: 5,527,342
[45] Date of Patent: Jun. 18, 1996

[54] METHOD AND APPARATUS FOR SECURING SOFT TISSUES, TENDONS AND LIGAMENTS TO BONE

[76] Inventors: William S. Pietrzak, 1691 S. Meadow Dr.; Roy C. Wiley, 73 S. C.R.325 E.; David L. Ahlersmeyer, 2829 Tall Oak Trail, all of Warsaw, Ind. 46580

[21] Appl. No.: 167,532

[22] Filed: Dec. 14, 1993

[51] Int. Cl.⁶ .................................................... A61B 17/04
[52] U.S. Cl. ............................ 606/232; 606/75; 411/353; 411/517
[58] Field of Search ................................ 606/232, 72–75, 606/104, 176, 220; 411/457, 970, 517, 353

[56] References Cited

U.S. PATENT DOCUMENTS

| | | |
|---|---|---|
| 82,181 | 9/1868 | Tileston . |
| 431,175 | 7/1890 | Southwick . |
| 446,871 | 2/1891 | Lieb . |
| 758,881 | 5/1904 | Yost . |
| 887,074 | 5/1908 | Depage . |
| 1,425,199 | 8/1922 | Hartley . |
| 1,598,026 | 8/1926 | Thompson . |
| 1,617,818 | 2/1927 | Mackenzie . |
| 1,638,477 | 4/1926 | Dyer . |
| 1,670,521 | 5/1928 | Ray . |
| 2,065,325 | 12/1936 | Calhoun . |
| 2,134,765 | 11/1938 | Putnam . |
| 2,381,050 | 7/1945 | Hardinge . |
| 2,398,603 | 4/1946 | Soderberg . |
| 2,562,419 | 7/1951 | Ferris . |
| 2,570,465 | 9/1951 | Lundholm . |
| 2,741,289 | 4/1956 | Grow . |
| 2,818,753 | 1/1958 | Leggett . |
| 3,103,926 | 9/1963 | Cochran et al. . |
| 3,133,378 | 5/1964 | Poupitch . |
| 3,512,289 | 5/1970 | Hayes . |
| 3,535,751 | 10/1970 | Batchelor . |
| 3,716,058 | 2/1973 | Tanner, Jr. . |
| 3,727,611 | 4/1973 | Schultz . |
| 3,744,488 | 7/1973 | Cox . |
| 3,755,860 | 9/1973 | Schenk et al. . |
| 3,775,825 | 12/1973 | Wood et al. . |
| 3,883,901 | 5/1975 | Coquard et al. . |
| 4,007,732 | 2/1977 | Kvavle et al. . |
| 4,013,071 | 3/1977 | Rosenberg . |

(List continued on next page.)

FOREIGN PATENT DOCUMENTS

| | | |
|---|---|---|
| 581535 | 2/1989 | Australia . |
| 606949 | 2/1991 | Australia . |
| 612097 | 6/1991 | Australia . |
| 1252364 | 4/1989 | Canada . |
| 1258022 | 8/1989 | Canada . |
| 0059044A2 | 9/1982 | European Pat. Off. . |
| 0081857A1 | 6/1983 | European Pat. Off. . |
| 0126520A2 | 11/1984 | European Pat. Off. . |
| 0232049A1 | 8/1987 | European Pat. Off. . |
| 0241240A3 | 10/1987 | European Pat. Off. . |
| 0358372A1 | 3/1990 | European Pat. Off. . |
| 0373264A1 | 6/1990 | European Pat. Off. . |
| 0376641A1 | 7/1990 | European Pat. Off. . |
| 0442182A1 | 8/1991 | European Pat. Off. . |
| 2289152 | 5/1976 | France . |
| 2346591 | 10/1977 | France . |
| 2395738 | 1/1979 | France . |
| 3538238A1 | 9/1986 | Germany . |
| 3630390A1 | 3/1987 | Germany . |
| 2078528 | 1/1982 | United Kingdom . |
| 2084468 | 4/1982 | United Kingdom . |
| 2118662 | 11/1983 | United Kingdom . |

Primary Examiner—Gary Jackson
Attorney, Agent, or Firm—Harness, Dickey & Pierce

[57] ABSTRACT

An apparatus for securing soft tissues, tendons and ligaments to bone using a suture strand. The apparatus includes a spear member which is able to pierce and securely engage the bone. The spear member includes an eyelet which is able to carry the suture strand at a position along the midportion of the suture strand. The suture strand is secured to the bone upon engagement between the spear member and the bone. In addition, the ends of the suture strand are accessible to the surgeon so that they may be manipulated so as to secure the soft tissue to the bone.

30 Claims, 5 Drawing Sheets

U.S. PATENT DOCUMENTS

| | | |
|---|---|---|
| 4,047,524 | 9/1977 | Hall . |
| 4,091,880 | 5/1978 | Troutner . |
| 4,124,026 | 11/1978 | Berner . |
| 4,140,111 | 2/1979 | Morrill . |
| 4,146,022 | 3/1979 | Johnson et al. . |
| 4,243,037 | 1/1981 | Smith . |
| 4,244,370 | 1/1981 | Furlow et al. . |
| 4,245,545 | 1/1981 | Freeman . |
| 4,257,411 | 3/1981 | Cho . |
| 4,263,903 | 4/1981 | Griggs . |
| 4,278,091 | 7/1981 | Borzone . |
| 4,287,807 | 9/1981 | Pacharis et al. . |
| 4,301,551 | 11/1981 | Dore et al. . |
| 4,337,773 | 7/1982 | Raftopoulos et al. . |
| 4,372,718 | 2/1983 | Zaydel . |
| 4,383,527 | 5/1983 | Asnis et al. . |
| 4,388,921 | 6/1983 | Sutter et al. . |
| 4,400,833 | 8/1983 | Kurland . |
| 4,409,974 | 10/1983 | Freedland . |
| 4,414,967 | 11/1983 | Shapiro . |
| 4,425,782 | 1/1984 | Todisco . |
| 4,438,769 | 3/1984 | Pratt et al. . |
| 4,456,006 | 6/1984 | Wevers et al. . |
| 4,467,478 | 8/1984 | Jurgutis . |
| 4,497,321 | 2/1985 | Fearing et al. . |
| 4,509,516 | 4/1985 | Richmond . |
| 4,535,768 | 8/1985 | Hourahane et al. . |
| 4,537,185 | 8/1985 | Stednitz . |
| 4,550,449 | 11/1985 | Tunc . |
| 4,570,624 | 2/1986 | Wu . |
| 4,590,928 | 5/1986 | Hunt et al. . |
| 4,592,346 | 6/1986 | Jurgutis . |
| 4,605,414 | 8/1986 | Czajka . |
| 4,627,425 | 12/1986 | Reese . |
| 4,632,100 | 12/1986 | Somers et al. ............................ 606/232 |
| 4,640,271 | 2/1987 | Lower . |
| 4,649,732 | 3/1987 | Molina . |
| 4,657,461 | 4/1987 | Smith . |
| 4,659,604 | 4/1987 | Lambuth . |
| 4,668,233 | 5/1987 | Seedhom et al. . |
| 4,669,473 | 6/1987 | Richards et al. . |
| 4,672,957 | 6/1987 | Hourahane . |
| 4,688,561 | 8/1987 | Reese . |
| 4,708,139 | 11/1987 | Dunbar, IV . |
| 4,711,234 | 12/1987 | Vives et al. . |
| 4,712,542 | 12/1987 | Daniel et al. . |
| 4,712,550 | 12/1987 | Sinnett . |
| 4,738,255 | 4/1988 | Goble et al. ............................ 606/232 |
| 4,739,751 | 4/1988 | Sapega et al. . |
| 4,741,330 | 5/1988 | Hayhurst ................................ 606/232 |
| 4,744,793 | 5/1988 | Parr et al. . |
| 4,759,765 | 7/1988 | Van Kampen . |
| 4,772,286 | 9/1988 | Goble et al. . |
| 4,773,417 | 9/1988 | Moore et al. . |
| 4,781,182 | 11/1988 | Purnell et al. . |
| 4,784,126 | 11/1988 | Hourahane . |
| 4,787,377 | 11/1988 | Laboureau . |
| 4,793,335 | 12/1988 | Frey et al. . |
| 4,823,780 | 4/1989 | Odensten et al. . |
| 4,826,375 | 5/1989 | Holton . |
| 4,834,752 | 5/1989 | Van Kampen . |
| 4,870,957 | 10/1989 | Goble et al. . |
| 4,878,915 | 11/1989 | Brantigan ................................ 623/17 |
| 4,898,156 | 2/1990 | Gatturna et al. . |
| 4,899,743 | 2/1990 | Nicholson et al. . |
| 4,901,711 | 2/1990 | Goble et al. . |
| 4,920,958 | 5/1990 | Walt et al. . |
| 4,927,421 | 5/1990 | Goble et al. . |
| 4,946,268 | 8/1990 | Li . |
| 4,950,270 | 8/1990 | Bowman et al. . |
| 4,960,420 | 10/1990 | Goble et al. . |
| 4,968,315 | 11/1990 | Gatturna . |
| 4,985,032 | 1/1991 | Goble . |
| 4,988,351 | 1/1991 | Paulos et al. . |
| 4,997,433 | 3/1991 | Goble et al. . |
| 5,002,550 | 3/1991 | Li . |
| 5,013,316 | 5/1991 | Goble et al. . |
| 5,037,422 | 8/1991 | Hayhurst et al. . |
| 5,037,426 | 8/1991 | Goble et al. . |
| 5,046,513 | 9/1991 | Gatturna et al. . |
| 5,100,417 | 3/1992 | Cerier et al. . |
| 5,102,421 | 4/1992 | Anspach et al. . |
| 5,141,520 | 8/1992 | Goble et al. . |
| 5,192,303 | 3/1993 | Gatturna et al. . |
| 5,200,336 | 4/1993 | Kong et al. . |
| 5,207,679 | 5/1993 | Li . |
| 5,217,486 | 6/1993 | Rice et al. . |
| 5,224,946 | 7/1993 | Hayhurst et al. . |
| 5,236,445 | 8/1993 | Hayhurst et al. . |
| 5,258,016 | 11/1993 | DiPoto et al. ............................ 606/232 |
| 5,336,240 | 8/1994 | Metzler et al. ............................ 623/232 |

METHOD AND APPARATUS FOR SECURING SOFT TISSUES, TENDONS AND LIGAMENTS TO BONE

BACKGROUND OF THE INVENTION

1. Field of the Invention

This invention relates to the orthopedic surgical procedures, and more particularly to a method and apparatus for securing soft tissues, tendons and ligaments to bone during orthopedic surgical repair procedures.

2. Description of the Related Art

It is often necessary to secure soft tissues, tendons and ligaments to bone during orthopedic surgical repair procedures. In the past, various methods and devices have been developed to accomplish this soft tissue attachment. In one known procedure, the orthopedic surgeon would make large incisions into the soft tissue to expose the bone, drill angled holes through the bone, and then threading sutures through the holes in order to finally achieve ligament attachment. This known procedure was extremely complex and time consuming.

Due to the difficulties and complications associated with the previous procedures, alternative methods and devices have been developed. One class of devices for attaching soft tissues to bone, developed to overcome some of the disadvantages of the previous devices and procedures, are suture anchors. A suture anchor generally comprises an anchor member which can be seated within the bone. A suture strand is secured to the anchor member and, thus, is available for aiding in attaching soft tissues, tendons and ligaments at the bone. Suture anchors usually require less complex surgical procedures than those associated with earlier methods for attaching soft tissue to bone.

In utilizing some of the known suture anchors, an anchor receiving hole must first be pre-drilled into the bone before the suture anchor can be seated therein. The suture anchor device disclosed in U.S. Pat. No. 5,141,520 to Goble et al. eliminates such a pre-drilling step. Generally, this reference teaches a pointed suture anchor that is forcefully driven into the bone. One arm, or end, of a suture strand is secured within a bore of the suture anchor. A force is then applied to the suture anchor through a driver member which is able to removably engage the suture anchor. After the suture anchor has been driven into the bone, the driver member is withdrawn, leaving the suture anchor seated within the bone. Once this seating procedure has been completed, the other arm of the suture strand extends away from the suture anchor and remains available for attaching various soft tissues, tendons and ligaments to the bone.

A disadvantage associated with the suture anchor disclosed in U.S. Pat. No. 5,141,520 relates to the fact that the suture anchor receives and retains only one of the two arms of the suture strand. That is, only a single arm of the suture strand extends out from the suture anchor once the suture anchor has been seated within the bone. Accordingly, two separate suture anchors are generally required in order to provide the two arms which are generally needed for forming a knot. It will therefore be appreciated that it is desirable to have a single suture anchor in which both arms of the suture strand extend from the anchor, since the accessibility of each of the arms would facilitate the formation of knots for attachment procedures.

SUMMARY OF THE INVENTION

One feature of the present invention relates to an apparatus for securing soft tissue to a bone using a suture strand. The apparatus comprises means for carrying the suture strand at a position along the midpoint of the suture strand. The apparatus also includes means for piercing and securely engaging the bone which is in mechanical communication with the means for carrying the suture strand. The apparatus is operable to permit the suture strand to be secured to the bone while the ends of the suture strand may be manipulated so as to secure the soft tissue to the bone.

Another feature of the present invention relates to a method for securing a suture strand, having a first end and a second end and a midportion disposed between the first and second ends, at a bone during orthopedic surgical repair procedures. The method includes the step of threading the suture strand through an eyelet in an anchor so that the midportion of the suture strand is disposed within the eyelet. The method also includes the step of imbedding at least a portion of the anchor within the bone so that the midportion of the suture strand is held by the anchor at the bone.

Accordingly, it is a general object of the present invention to provide a method and apparatus for attaching a suture to bone, and more particularly to provide a method and apparatus for attaching soft tissues, tendons and ligaments to bone during orthopedic surgical repair procedures.

A further object of the present invention is to provide a method and apparatus for attaching suture to bone whereby a central portion of a suture strand is securely anchored within a bone, leaving the two ends of the strand extending outwardly to facilitate the formation of knots for attachment procedures.

Another object of the present invention is to provide a method and apparatus for attaching soft tissues, tendons and ligaments to bone which reduces the number of suture anchors required during orthopedic surgical repair procedures.

A further object of the present invention is to provide a method and apparatus for securing a suture to a bone by way of an anchoring system which is relatively easy to manufacture.

A further related object of the present invention is to provide a method and apparatus for securing a suture to a bone which is relatively simple and low in cost, yet which is highly effective for attaching soft tissues, tendons and ligaments during orthopedic surgical repair procedures.

A further object of the present invention is to provide a method and apparatus to secure a suture to bone without the need to pre-drill the bone nor require the use of a drill to install the anchor.

A further object of the present invention is to provide a method and apparatus for securing a suture to bone in which the position of the suture is able to be rotated after the suture has been secured to the bone.

A further object of the present invention is to provide a method and apparatus to secure one or more sutures to bone which may be used to secure the soft tissue to the bone.

A further object is to provide a means to attach more than one suture to the anchor.

BRIEF DESCRIPTION OF THE DRAWINGS

The structure and manner of operation of the present invention, together with the further objects and advantages thereof, may best be understood by reference to the following description taken in conjunction with the accompanying drawings, in which identical reference numerals identify similar elements, and in which:

FIGS. 9—11 are side elevational views of the apparatus for securing soft tissues, tendons and ligaments to bone shown in operative association with a driver instrument according to the teachings of one preferred embodiment of the present invention.

DESCRIPTION OF THE PREFERRED EMBODIMENTS

The following discussion of the preferred embodiments of the present invention is merely exemplary in nature. Accordingly, this discussion is in no way intended to limit the scope of the invention, application of the invention, or the uses of the invention.

Figure 1:
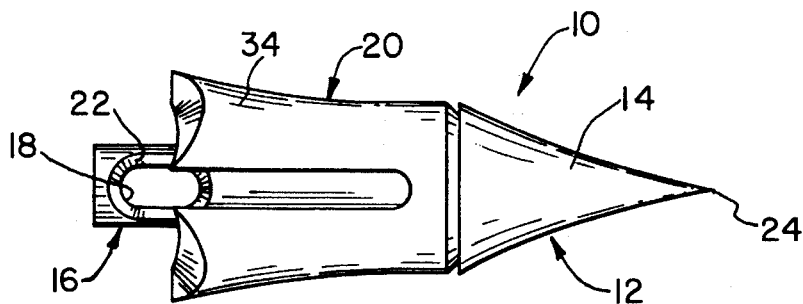
FIG. 1 is a side elevational view of the apparatus for securing soft tissues, tendons and ligaments to bone according to the teachings of one preferred embodiment of the present invention.

Referring initially to FIG. 1, a suture anchor 10 according to the first preferred embodiment of the present invention is shown. The suture anchor 10 is used for attaching soft tissues, tendons and ligaments to bone during orthopedic surgical repair procedures. It will be understood, however, that the suture anchor 10 may also be used with other types of surgical procedures as well. To provide means for piercing and securely engaging the bone, the suture anchor 10 comprises a spear member 12. The spear member 12 has a generally cone-shaped head portion 14 which is used for piercing the bone to which the soft tissue is to be secured, and a shaft portion 16 with an oval eyelet 18 therethrough for receiving and holding a suture strand or strands. To provide means for retaining the spear member 12 within the bone, the suture anchor 10 further comprises a collar member 20. The collar member 20 is used for retaining the suture anchor 10 in place, once it has been driven into the bone, by lodging within the bone in a manner to resist removal of the suture anchor 10. The suture anchor 10 and its component parts are more fully described below.

Figures 2, 3:
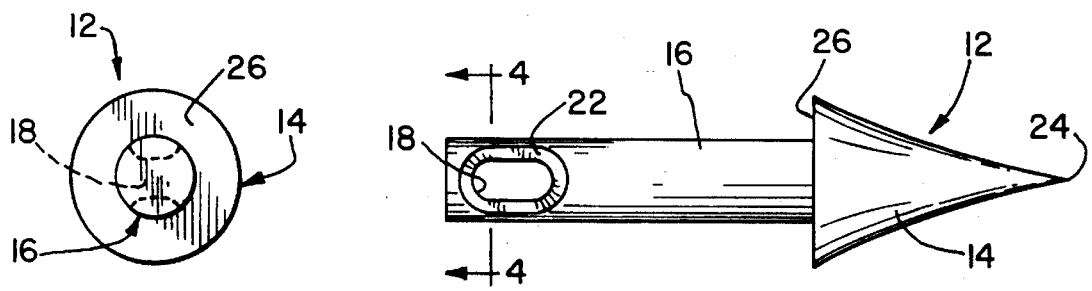
FIG. 2 is a side elevational view of a spear member of the apparatus for securing soft tissues, tendons and ligaments to bone as shown in FIG. 1 according to the teachings of one preferred embodiment of the present invention.
FIG. 3 is a rear elevational view of the spear member of the apparatus for securing soft tissues, tendons and ligaments to bone as shown in FIG. 1 according to the teachings of one preferred embodiment of the present invention.
Figure 4:
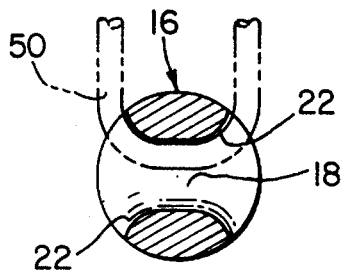
FIG. 4 is an enlarged sectional view of a shaft of the spear member of the apparatus for securing soft tissues, tendons and ligaments to bone according to the teachings of one preferred embodiment of the present invention taken along the lines 4—4 of FIG. 2.
Figure 5:
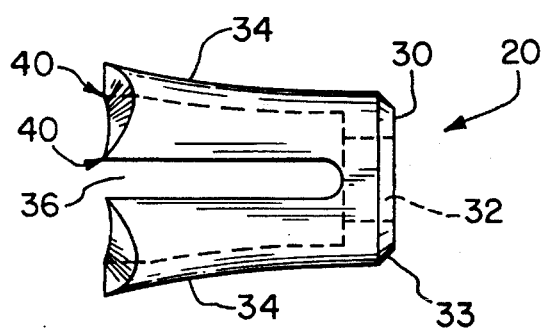
FIG. 5 is a side elevational view of a collar member of the apparatus for securing soft tissues, tendons and ligaments to bone as shown in FIG. 1 according to the teachings of one preferred embodiment of the present invention.
Figure 6:
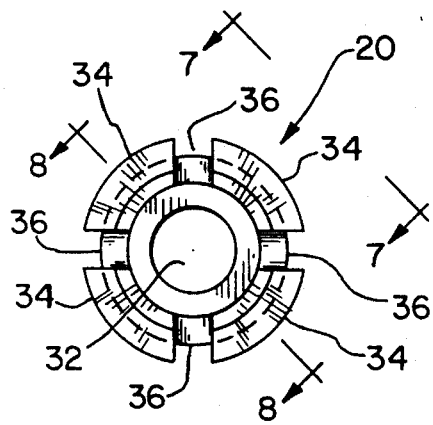
FIG. 6 is a rear elevational view of the collar member of the apparatus for securing soft tissues, tendons and ligaments to bone as shown in FIG. 1 according to the teachings of one preferred embodiment of the present invention.
Figure 7:
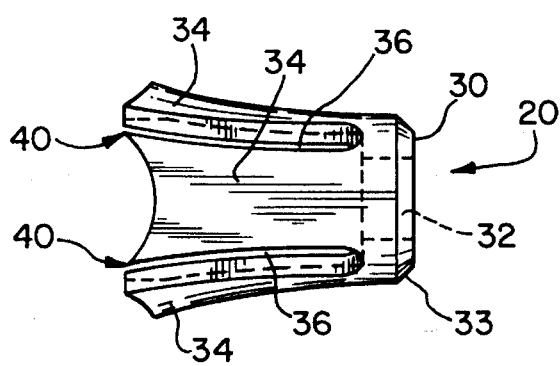
FIG. 7 is a side elevational view of the collar member of the apparatus for securing soft tissues, tendons and ligaments to bone according to the teachings of one preferred embodiment of the present invention taken along the direction of the lines 7—7 of FIG. 6.
Figure 8:
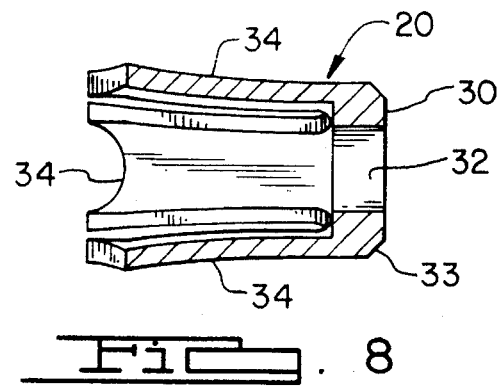
FIG. 8 is a sectional view of the collar member of the apparatus for securing soft tissues, tendons and ligaments to bone according to the teachings of one preferred embodiment of the present invention taken along the lines 8—8 of FIG. 6.
Figure 12:
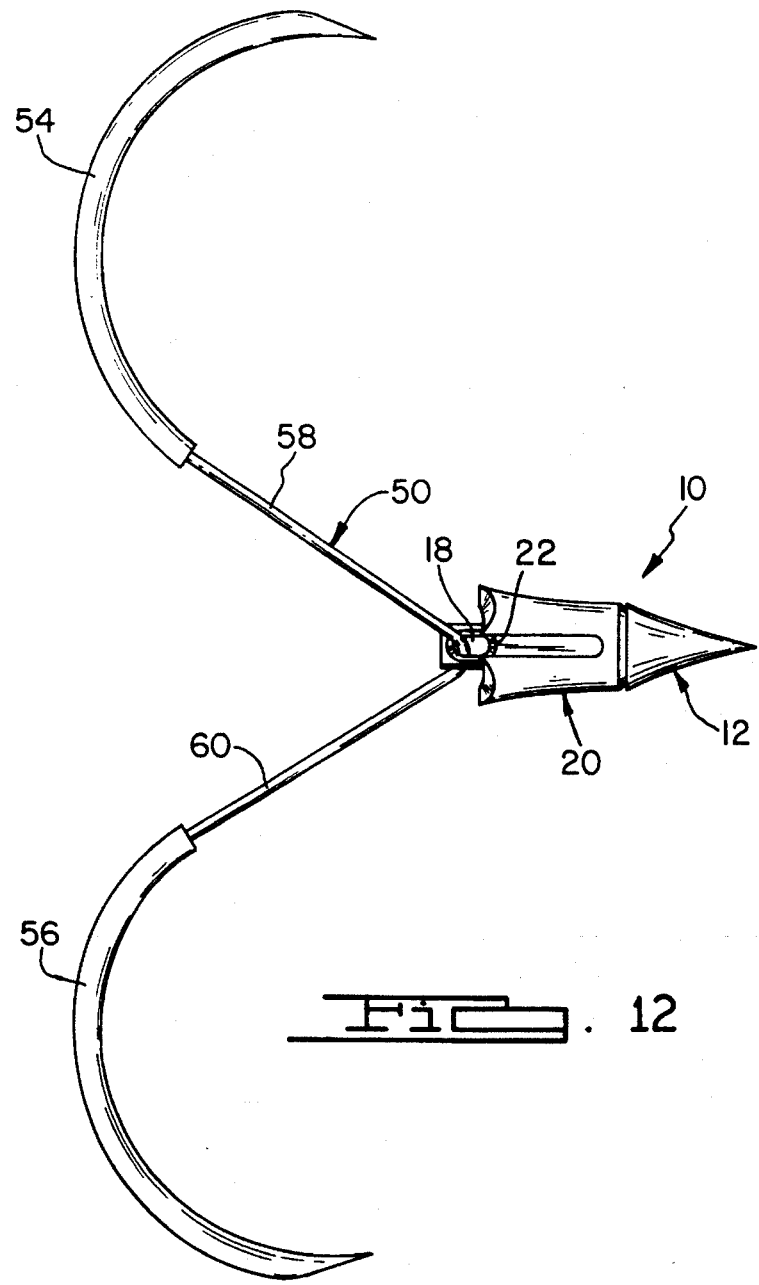
FIG. 12 is a side elevational view of the apparatus for securing soft tissues, tendons and ligaments to bone shown in operative association with a suture strand according to the teachings of one preferred embodiment of the present invention.
Figure 13:
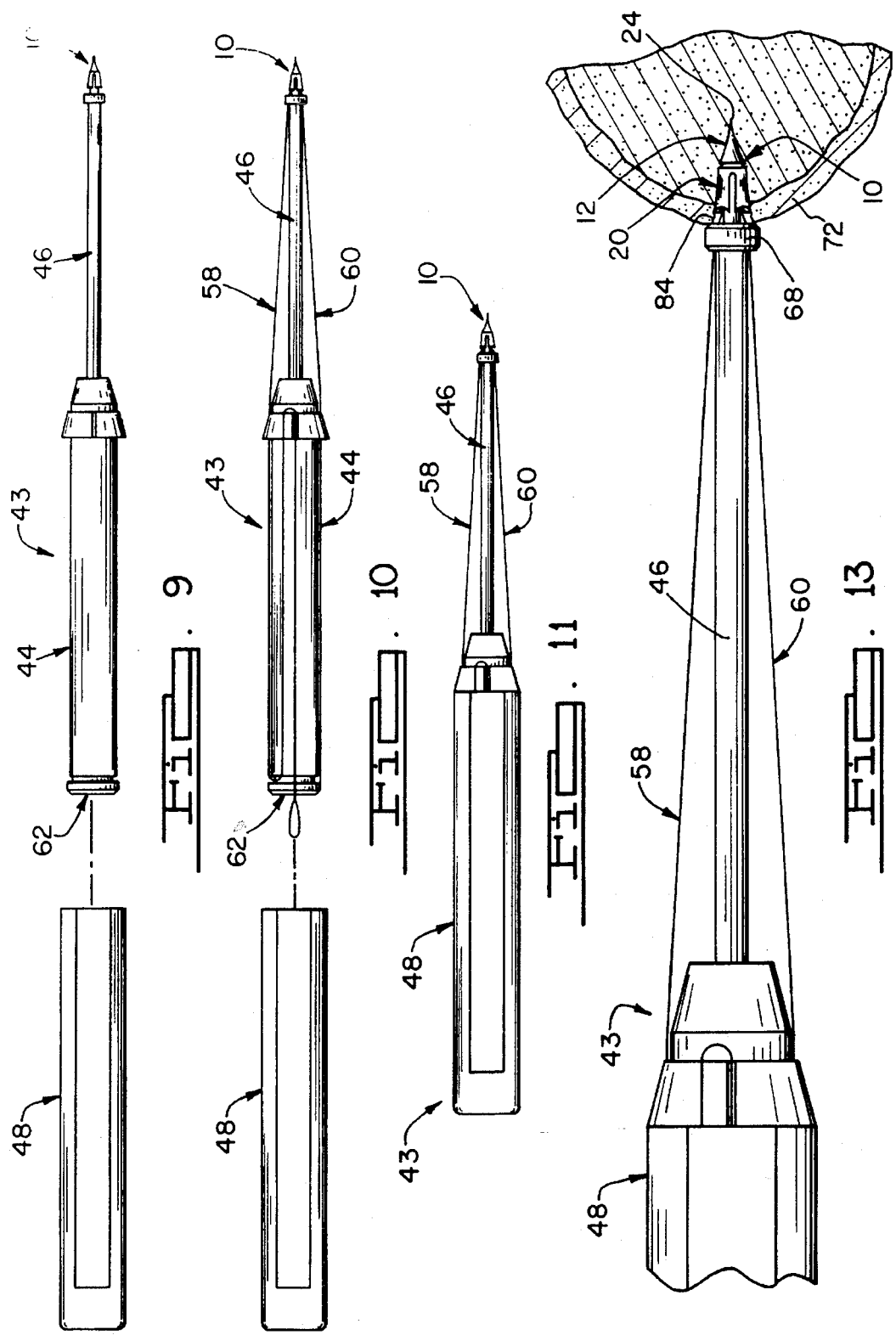
FIG. 13 is a side elevational view of the apparatus for securing soft tissues, tendons and ligaments to bone mounted on the forward end of a driver instrument and shown entering a section of bone according to the teachings of one preferred embodiment of the present invention.

The spear member 12 of the suture anchor 10 will now be described with additional reference to FIGS. 2–4. The shaft portion 16 of the spear member 12 is generally cylindrical in shape and has the eyelet 18, or bore, formed radially therethrough proximate one of its ends. The eyelet 18 may be oval, round or other suitable shapes and is of a sufficient size to permit suture strand or strands to pass therethrough. The circumference of each outer end of the eyelet 18 is chamfered or grounded to provide a bevel portion 22. It should be appreciated that the bevel portion 22 provides a generally smooth surface for contacting suture strand which has been passed through the eyelet 18. The eyelet 18 is located on the shaft portion 16 of the spear member 12 such that the transverse axis of the eyelet 18 intersect the longitudinal axis of the spear member 12.

The generally cone-shaped head portion 14 of the spear member 12 is located at an end of the shaft portion 16 opposite the end having the eyelet 18. As best shown in FIGS. 1 and 2, the apex of the cone-shaped head portion 14 is a point 24 which is suitable for piercing and being driven into bone. The diameter of the cone-shaped head portion 14 increases, when viewed along a longitudinal direction rearwardly from the point 24 towards the shaft portion 16. The cone angle along this region is preferably about 30 degrees. The diameter of the cone-shaped head portion 14 increases at a greater rate along approximately the rearward half thereof, when viewed along the same longitudinal direction. Thus, the rearward half of the cone-shaped head portion 14 arcs outwardly from the central longitudinal axis of the spear member 12. As shown in FIGS. 2 and 3, the base 26 of the cone-shaped head portion 14 is a ring-shaped planar surface which is oriented substantially perpendicular to the longitudinal axis of the shaft portion 16.

Preferably, the cone-shaped head portion 14 is formed integrally with the shaft portion 16 of the spear member 12. Alternatively, the cone-shaped head portion 14 and the shaft portion 16 may initially be formed separately and then subsequently attached to one another by any suitable means.

The collar member 20 of the suture anchor 10 will now be described with particular reference to FIG. 1 and FIGS. 5–8. The collar member 20 is provided with a ring-shaped generally planar forward surface 30 which is adapted to bear against, and mate with, the base 26 of the cone-shaped head portion 14 of the spear member 12. A circular bore 32 is located centrally through the planar forward surface 30 and is adapted to receive the shaft portion 16 of the spear member 12 therethrough. The circumference of the planar forward surface 30 may be, but is not necessarily, chamfered to formed a beveled outer rim portion 33.

Four separate flanges 34 extend rearwardly from the planar forward surface 30 of the collar member 20 as shown in FIGS. 5–8. The flanges 34 are separated from one another by longitudinally extending slots 36. The portions of the flanges 34 which are proximate to the planar forward surface 30 run generally parallel to the central longitudinal axis of the collar member 20. Each of the flanges 34 arcs generally outward from the central longitudinal axis as the flange 34 extends in a direction away from the planar forward surface 30. The lateral width of each of the flanges 34 increases as the flange 34 extends in a direction away from the planar forward surface 30. The extreme rearwardmost end of each of the flanges 34 curves away from the planar forward surface 30 in the form a shallow C-shape, thereby providing two trailing tips 40 for each flange 34.

As set forth above, the collar member 20 is rotatably fitted over the shaft portion 16 of the spear member 12 to form the assembled suture anchor 10 as shown in FIG. 1. While there is no need to permanently secure the collar member 20 to the spear member 12, the planar forward surface 30 may nevertheless be securely attached to the base 26 of the cone-shaped head member 14 of the spear member 12 by any suitable means. It will be appreciated, however, that by permitting the spear member 12 to freely rotate with respect to collar member 20, the suture strand 50 can be rotated by the surgeon after implantation to a position where the forces acting on the suture strand 50 by the suture anchor 10 are more evenly distributed around the region of the shaft portion 16 adjacent to the eyelet 18. Such a position of the suture stand 50 is shown in FIG. 4.

In addition, it should also be appreciated that the two-piece constructure of the suture anchor 10, affords machining advantages over a single-piece suture anchor. That is, it is easier to machine each of these components separately and to subsequently assemble them together, as opposed to machining the same basic structural features from a single piece of material. Any known materials suitable for orthopedic anchor devices may be employed to construct the suture anchor 10 of the present invention. Preferably, the suture anchor 10 is formed from a metallic material possessing sufficient strength to penetrate the bone. Such materials include 316 LVM stainless steel, CoCrMo alloy, Nitinol alloy, or other suitable materials.

To provide means for driving the suture anchor 10 into bone, a driver instrument 43 is provided. The driver instrument 43 generally comprises a plastic handle portion 44 and a metallic driver stem 46 which is securely fixed to the handle portion 44. Additionally, a plastic driver handle cover 48 is provided which slides over, and attaches to, the driver handle portion 44. As will be more fully discussed below, the driver instrument 43 is operable to receive the suture anchor 10 at the forward end of the driver stem 46 so as to permit the driver instrument 43 to drive the suture anchor 10 into the bone.

The operation of the driver instrument 43 will now be described. Prior to mounting the suture anchor 10 on the driver stem 46, a suture strand 50, having curved needles 54 and 56 attached at the end of each free arm 58 and 60, respectively, is threaded and looped through the eyelet 18. Alternatively, it may be necessary to attach the needles 54 and 56 to the suture strand 50 after passing the suture strand 50 through the eyelet 18 due to the large diameter of the needles 54 and 56 relative to that of the eyelet 18. The suture anchor 10 is then mounted on the end of the driver stem 46 and the suture strand arms 58 and 60 are routed through channels formed in the handle portion 44 as shown in FIG. 10. The curved needles 54 and 56 are then inserted through an opening 62 formed in one end of the handle portion 44 and stored within a channel (not shown) which extends from the opening 62 inwardly into the handle portion 44. Preferably, the channel includes a foam insert which is operable to receive the needles 54 and 56 during use as well as during packaging and shipping. Finally, the driver handle cover 48 is slid over the handle portion 44 and is secured thereto, as by way of a set of mating threads (not shown) formed about a portion of the handle portion 44 and within a portion of the driver handle cover 48. In this manner, the suture arms 58 and 60 and the curved needles 54 and 56 are retained within the handle portion 44 by the driver handle cover 48.

Figure 14:
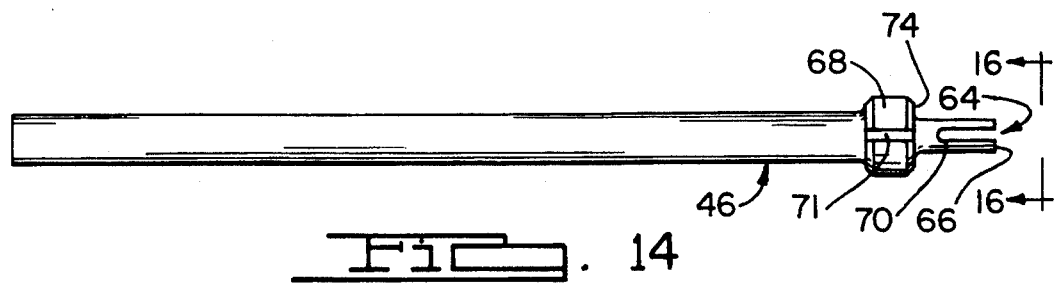
FIG. 14 is an enlarged side elevational view of the stem of the driver instrument shown in FIG. 13 according to the teachings of one preferred embodiment of the present invention.
Figure 15:
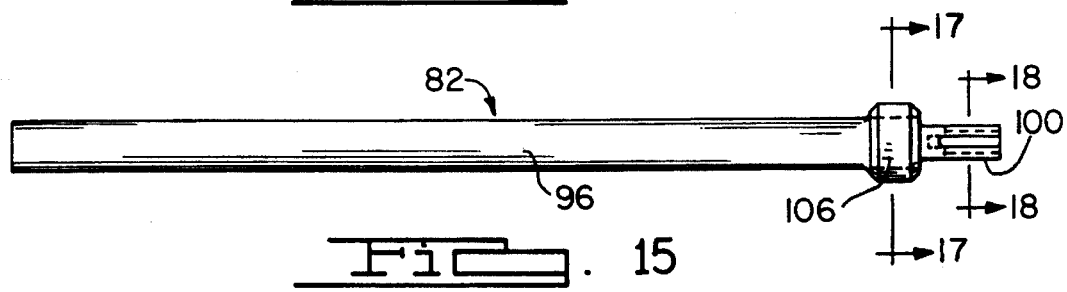
FIG. 15 is an enlarged side elevational view of a stem of the driver instrument shown in FIG. 13 according to the teachings of a second preferred embodiment of the present invention.
Figure 16:
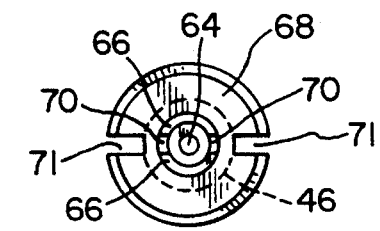
FIG. 16 is an enlarged front elevational view of the stem of the driver instrument according to the teachings of one preferred embodiment of the present invention taken along the direction of the lines 16—16 of FIG. 14.
Figure 17:
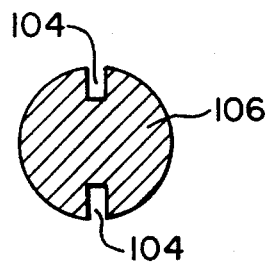
FIG. 17 is an enlarged sectional view of the stem of the driver instrument according to the teachings of a second preferred embodiment of the present invention taken along the lines 17—17 of FIG. 15.
Figure 18:
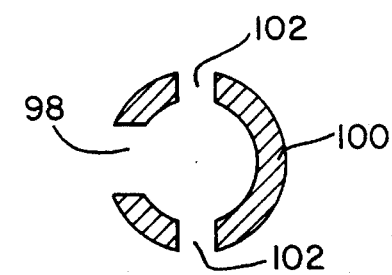
FIG. 18 is an enlarged sectional view of the stem of the driver instrument according to the teachings of a second preferred embodiment of the present invention taken along the lines 18—18 of FIG. 15.
Figure 19:
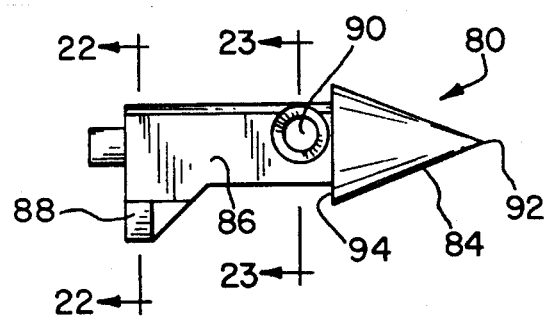
FIG. 19 is a side elevational view of an apparatus for securing soft tissues, tendons and ligaments to bone according to the teachings of a second preferred embodiment of the present invention.
Figure 20:
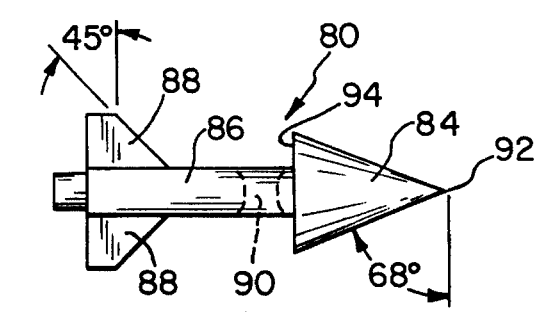
FIG. 20 is a top plan view of the apparatus for securing soft tissues, tendons and ligaments to bone shown in FIG. 19 according to the teachings of a second preferred embodiment of the present invention.
Figure 21:
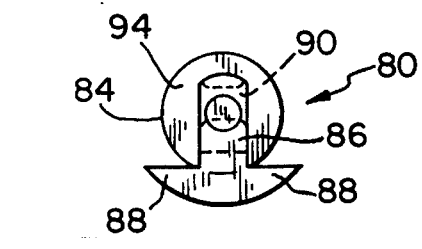
FIG. 21 is a rear elevational view of the apparatus for securing soft tissues, tendons and ligaments to bone shown in FIG. 19 according to the teachings of a second preferred embodiment of the present invention.
Figure 22:
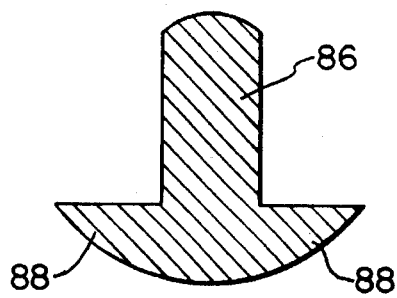
FIG. 22 is an enlarged sectional view of the apparatus for securing soft tissues, tendons and ligaments to bone according to the teachings of a second preferred embodiment of the present invention taken along the lines 22—22 of FIG. 19.
Figure 23:
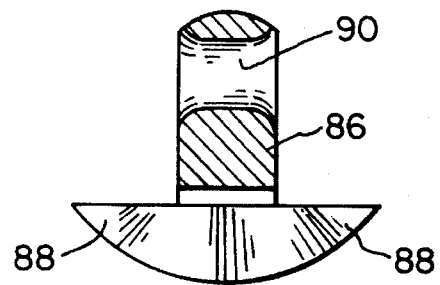
FIG. 23 is an enlarged sectional view of the apparatus for securing soft tissues, tendons and ligaments to bone according to the teachings of a second preferred embodiment of the present invention taken along the lines 23—23 of FIG. 19.

FIGS. 14 and 16 show the driver stem 46 in greater detail. The driver stem 46 includes a circular bore 64 which extends from the forwardmost end 66 of the driver stem 46 toward a driver collar portion 68. A pair of opposing slots 70 also extend from the forwardmost end of the driver stem 46 in a direction toward the driver collar portion 68. The suture anchor 10 can therefore be received by the driver stem 46 by inserting the shaft portion 16 of the suture anchor 10 into the bore 64 of the driver stem 46. When inserting the shaft portion 16 in this manner, the eyelet 18 of the shaft portion 16 is preferably aligned with the slots 70 so that the suture arms 58 and 60, threaded through the eyelet 18 as described above, can extend out of the bore 64 and along each side of the driver stem 46. Another pair of longitudinal slots 71 are provided along each side of the driver collar portion 68, in line with the slots 70, for receiving and guiding the suture arms 58 and 60 as they are routed back towards the driver handle portion 44 of the driver instrument 43. This construction allows the suture strand 50 to be effectively routed between the suture anchor 10 and the driver instrument 43 while protecting the suture strand 50 from being pinched or cut during insertion of the suture anchor 10 into bone as described below.

As will be appreciated by those skilled in the art, it is preferable that the shaft portion 16 of the suture anchor 10 fit snugly, in a rigid and secure fashion, within the bore 64 of the driver stem 46. This is because it is desirable to efficiently transmit force from the driver 43 to the suture anchor 10 to effectively drive the suture anchor 10 into the bone.

The method of the present invention will now be described. Initially, the suture anchor 10 and driver instrument 43 are assembled as described above and shown in FIG. 11. The point 24 of the suture anchor 10 is placed against the outer surface of the bone 72 at the position where suture attachment is desired. A force is then applied against the rearwardmost end of the driver handle cover 48 which is transmitted through the driver instrument 43 to the suture anchor 10 causing the point 24 to pierce into the cortex of the bone 72. The suture anchor 10 is then driven deeper into the bone 72 upon applying additional force through the driver instrument 43. As the collar portion 20 passes through the cortex, the flanges 34 flex inward somewhat. When the forward face 74 of the driver collar portion 68 contacts the outer surface of the bone 72, the suture anchor 10 has reached its ultimate depth within the bone 72. At that point, the flanges 34, including the trailing tips 40, of the collar member 20 are flexed outwardly somewhat, due to the elasticity of the material, and are lodged within the bone 72. The flanges 34 therefore provide resistance to forces which tends to pull the suture anchor 10 in a direction out of the bone 72. The driver instrument 43 is then withdrawn by first removing the outer sleeve 48 from the driver handle 44. The two arms 58 and 60 of the suture strand 50 as well as the curved needles 54 and 56 can then be removed from the bore 62 of the driver handle 44. Finally, the driver handle 44 is removed from the suture anchor 10 leaving the suture anchor 10 lodged within the bone 72.

An alternative embodiment of the invention, shown in FIGS. 15 and 17–23, provides a single piece suture anchor 80 and a driver instrument 82 for attaching soft tissues, tendons and ligaments to bone during orthopedic surgical repair procedures. The structure and method of use of the suture anchor 80 and driver instrument 82 is similar in certain respects to that of the first preferred embodiment set forth above. Accordingly, the following description focuses on aspects of the second preferred embodiment which differ from the first preferred embodiment described above. Those features or procedures which are not discussed below may be assumed to be similar to the features and procedures detailed with respect to the first preferred embodiment set forth and described above.

The suture anchor 80 according to the second preferred embodiment of the present invention is provided with a regular cone-shaped head 84 which is integrally formed with a body portion 86. A plurality of fins 88 extend from the body portion 86. An eyelet 90 extends through the body portion 86 of the suture anchor 80 and is adapted to receive a suture strand therethrough. It should be noted that the transverse axis running centrally through the eyelet 90, perpendicular to the plane of the body portion 86, is substantially offset from the longitudinal axis running centrally through the cone-shaped head portion 84 in a direction extending from its point 92 to the centerpoint of its base 94. Such offset between the transverse axis of the eyelet 90 and the cone-shaped leading head 84 causes the suture anchor 80 to cant or tilt within the bone 72 when the suture strand held within the eyelet 90 encounters a force tending to pull the suture anchor 80 out of the bone 72. This canting effect further secures the suture anchor 80 to the bone 72 and thereby increasing the resistance of the suture anchor 80 to removal.

The driver instrument 82 which is used for implanting the suture anchor 80 within the bone 72 is substantially similar to that of the first preferred embodiment described above. However, the driver stem 96 is adapted to receive the shape of the body portion 86 of the suture anchor 80. In particular, a slot 98 is formed in the forwardmost portion 100 of the driver stem 96 to accommodate the fins 88 of the suture anchor 80. In addition, additional slots 102 are provided in the forwardmost portion 100 for aligning with the eyelet 90 of the suture anchor 80 in order that suture strand may pass therethrough and extend upward through slots 104 of the driver collar 106 in route toward the driver handle 44. In contrast to the first preferred embodiment 10, once the suture anchor 80 of the second preferred embodiment 80 is driven into bone, the driver handle 44 and cover 48 can be turned, thereby turning driver instrument 82 and anchor 80, preferably, approximately 90° or one-quarter revolution. This has the effect of embedding the fins 88 beneath virgin cortical bone, providing further hinderance for removal of the implanted anchor 80.

Figure 24:
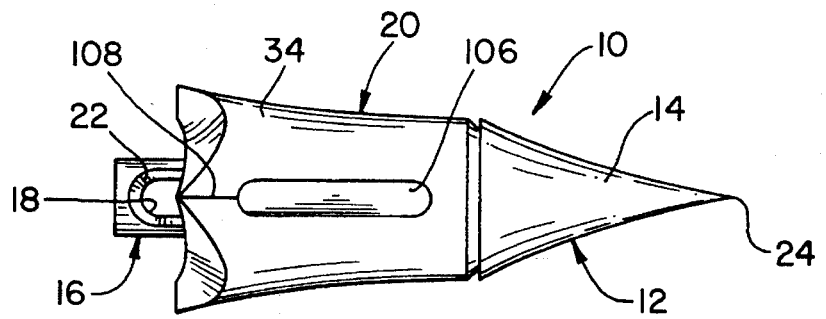
FIG. 24 is a side elevational view of the apparatus for securing soft tissues, tendons and ligaments to bone as shown in FIG. 1 according to the teachings of another preferred embodiment of the present invention.

A further embodiment of the present invention is shown in FIG. 24, in which the elements that are similar to the elements associated with the first preferred embodiment of the present invention have the same reference numerals. In this embodiment, the collar member 20 includes two pairs of diametrically opposed apertures 106 in which the diametrically opposing pairs of apertures are formed simultaneously. The apertures 106 are used to receive and capture bony tissue within the suture anchor 10 as the suture anchor 10 is driven into the bone as well as to enhance the deformability of the collar member 20 adjacent to the apertures 106. The apertures 106 are formed by a wire EDM process and therefore the collar member 20 also includes a small slit 108 which is formed as a result of the formation of each of the opposing pairs of apertures 106. The slit 108 is relatively small in thickness depending upon the wire used (approximately 0.004" to 0.020") and therefore does not influence the deformability of the collar member 20 at its trailing end. Because the suture anchor 10 receives and captures bony tissue in this manner, the suture anchor 10 according to this embodiment is able to provide an additional mechanism for resisting removal of the suture anchor 10 from the bone. In addition, because the size of the slit 108 is minimized, the trailing edge of the collar member 20 maintains substantially all of its surface to provide further resistance to the removal of the suture anchor 10.

Figure 25:
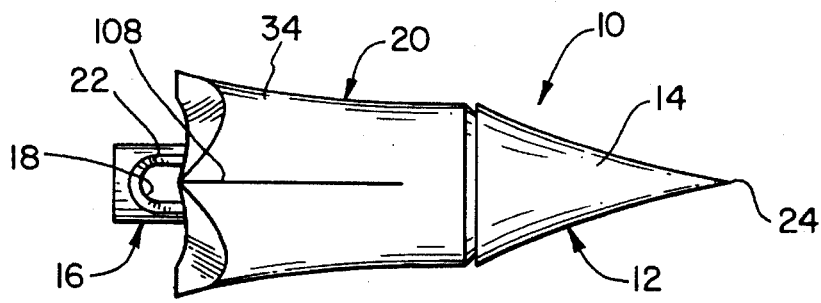
FIG. 25 is a side elevational view of the apparatus for securing soft tissues, tendons and ligaments to bone as shown in FIG. 1 according to another preferred embodiment of the present invention.

A further embodiment of the present invention is shown in FIG. 25, in which the elements that are similar to the elements that are shown in FIG. 24 have the same reference numerals. In the embodiment shown in FIG. 25, the collar member 20 includes a plurality of slits 108 which are used to form the flanges 34 in much the same manner as shown in FIG. 25. However, the suture anchor 10 shown in FIG. 24 does not include a plurality of apertures 106 which are present in the suture anchor 10 shown in FIG. 25.

Figure 26:
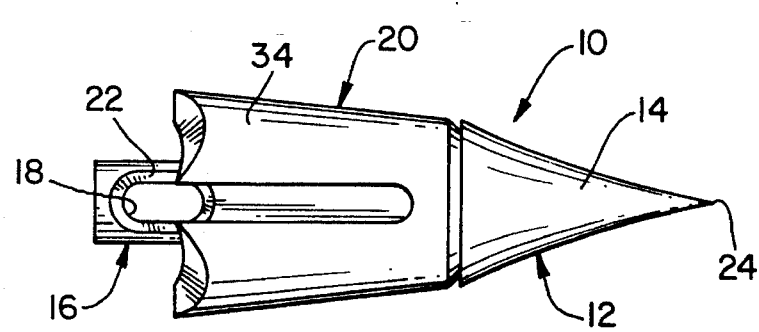
FIG. 26 is a side elevational view of the apparatus for securing soft tissues, tendons and ligaments to bone as shown in FIG. 1 according to the teachings of yet another preferred embodiment of the present invention.

Another embodiment of the present invention is shown in FIG. 26, in which the elements that are similar to the elements associated with the first preferred embodiment have the same reference numerals. In the embodiment shown in FIG. 26, the flanges 34 of the collar member 20 are configured to form a taper. However, the taper is such that the flanges 34 extend in a substantially straight direction and therefore do not have the curved configuration that is shown in FIG. 1. While the collar member 20 is indicated as being formed by a single straight taper, it will be appreciated that the collar member 20 may be formed by two or more straight tapered segments that intersect.

Those skilled in the art can now appreciate from the foregoing description that the broad teachings of the present invention can be implemented in a variety of forms. Therefore, while this invention has been described in connection with particular examples thereof, the true scope of the invention should not be so limited. For example, other suitable shapes and sizes may be employed for the suture anchor so long as the suture anchor performs substantially the same function as described. In this regard, the collar of the suture anchor may be of different configurations as may be the spear member. In addition, the shape and size of the collar member may be selected to accommodate the particular needs of a given application as well as the particular characteristics of a given patient. The number of pieces which constitute the suture anchor may also vary, and the suture anchor may be treated in such a manner to improve various physical characteristics such as lubricity (e.g., such as by nitriding). The suture anchor may also be used to accommodate more than one suture strand. Other modifications will become apparent to those skilled in the art.

What is claimed is:

1. An apparatus for anchoring a suture strand to a bone, said suture strand having a first end, a second end and a midportion disposed between the first and second ends, said apparatus comprising:

means for carrying the suture strand at a position along the midportion of the suture strand;

means in mechanical cooperation with said carrying means, for piercing and securely engaging the bone having a piercing portion; and means in mechanical cooperation with said carrying means, for retaining within the bone said means for piercing and securely engaging the bone, said means for retaining being operable to secure said means for carrying said suture strand and said piercing portion to the bone, said means for retaining being constructed separately from said piercing portion of said means for piercing and securely engaging the bone;

whereby the suture strand is operable to be secured to the bone and the first and second ends of the suture strand is manipulated to secure the soft tissues to the bone.

2. The apparatus for anchoring a suture strand to a bone as set forth in claim 1, wherein said means for retaining is movably attached to said means for piercing.

3. The apparatus for anchoring a suture strand to a bone as set forth in claim 2, wherein said piercing portion includes a generally cone-shaped head portion, and wherein said means for carrying the suture strand includes a stem which extends from said generally cone-shaped head portion.

4. The apparatus for anchoring a suture strand to a bone as set forth in claim 3, wherein said means for retaining said means for piercing and securely engaging the bone includes a collar member engageable with said generally cone-shaped head portion.

5. The apparatus for anchoring a suture strand to bone as set forth in claim 4, wherein said collar member further include an aperture for receiving bone when said means for piercing and securely engaging the bone pierces the bone.

6. The apparatus for anchoring a suture strand to a bone as set forth in claim 4, wherein said collar member includes a plurality of flanges being operable to engage the bone in a manner to resist removal thereof.

7. The apparatus for anchoring a suture strand to bone as set forth in claim 5, wherein said flanges are substantially straight.

8. The apparatus for anchoring a suture strand to a bone as set forth in claim 4, wherein said generally cone-shaped head portion is integrally constructed with said stem, and wherein said collar member is constructed separately from said generally cone-shaped head portion and said stem.

9. The apparatus for anchoring a suture strand to a bone as set forth in claim 3, wherein said means for carrying the suture strand further includes an eyelet formed in said stem.

10. The apparatus for anchoring a suture strand to a bone as set forth in claim 9, wherein said eyelet includes a transverse axis which extends through said eyelet, said transverse axis of said eyelet intersecting a longitudinal axis running centrally through said generally cone-shaped head portion.

11. A method for securing soft tissues to a bone using a suture strand and a suture anchor, said suture anchor having a hole therein and said suture strand having a first end, a second end and a midportion disposed between the first and second ends, said suture anchor including a body portion and a retaining portion, said method comprising the steps of:

positioning said retaining portion on said body portion;

locating said suture strand within the hole in said suture anchor so that said midportion of said suture strand is disposed within said hole;

piercing the bone with the suture anchor thereby embedding at least a portion of said suture anchor within the bone so that said midportion of said suture strand is held by said suture anchor proximate to the bone; and attaching the soft tissues to the bone by manipulation of said first and second ends of said suture strand.

12. The method for securing soft tissues to a bone as set forth in claim 11, wherein said step of embedding at least a portion of said suture anchor within the bone includes the steps of:

mounting said suture anchor upon a driver instrument having a shaft;

routing the first and second ends of said suture strand along said shaft of said driver instrument; and applying a force through said driver instrument to said suture anchor thereby embedding said suture anchor in said bone.

13. The method for securing soft tissues to a bone as set forth in claim 12, wherein said step of embedding at least a portion of said suture anchor within said bone further includes the step of stowing said first and second ends of said suture strand in a cavity formed in a handle portion of said driver instrument.

14. The method for securing soft tissues to a bone as set forth in claim 11, wherein said step of embedding at least a portion of said suture anchor within said bone further includes the step of securing a cover member about said handle portion of said driver instrument thereby capturing at least a portion of said handle portion and said suture strand within said cover member.

15. The method for securing soft tissues to a bone as set forth in claim 11, wherein said suture anchor includes a generally cone-shaped head portion and a stem which extends from said generally cone-shaped head portion.

16. The method for securing soft tissues to a bone as set forth in claim 15, wherein said suture anchor includes a collar member which is operable to be disposed about said stem, said collar member being operable to engage said bone to prevent removal of said anchor.

17. An apparatus for anchoring a suture strand to a bone during orthopedic surgical repair procedures, said apparatus comprising:

an anchor including a body portion and a retaining portion, said retaining portion defining a flange slidably mounted on said body and being movable between a bone-passing position and a bone engaging position;

means in mechanical cooperation with said anchor for forcefully piercing the bone; and a suture strand operable to be secured to said anchor, said suture strand having a first end, a second end, and a midportion disposed therebetween;

wherein said midportion of said suture strand is operable to be held by said anchor within the bone; and wherein said first end and said second end of said suture strand are operable to attach the soft tissues to the bone.

18. The apparatus for anchoring a suture strand to a bone during orthopedic surgical repair procedures as set forth in claim 17, wherein said anchor includes:

a generally cone-shaped leading portion for piercing the bone;

a trailing body portion extending from said generally cone-shaped leading portion; and an eyelet in said trailing body portion and adapted to retain said midportion of said suture strand.

19. The apparatus for anchoring a suture strand to a bone during orthopedic surgical repair procedures as set forth in claim 18, wherein said eyelet is circular in shape.

20. The apparatus for anchoring a suture strand to a bone during orthopedic surgical repair procedures as set forth in claim 17, wherein said body portion has formed thereon a generally cone-shaped leading portion for piercing the bone, said retaining portion being fitted to and separable from said generally cone-shaped leading portion.

21. The apparatus for anchoring a suture strand to a bone during orthopedic surgical repair procedures as set forth in claim 21, wherein said generally cone-shaped leading portion is operable to rotate with respect to said collar member.

22. The apparatus for anchoring a suture strand to a bone during orthopedic surgical repair procedures as set forth in claim 21, wherein said flange is formed on said retaining portion.

23. The apparatus for anchoring a suture strand to a bone during orthopedic surgical repair procedures as set forth in claim 22, wherein said flange is formed by a C-shaped surface on said collar member.

24. An apparatus for securing soft tissues to a bone using a suture strand, said suture strand having a first end, a second end and a midportion disposed between the first and second ends, said apparatus comprising:

means for carrying the suture strand at a position along the midportion of the suture strand;

means in mechanical cooperation with said carrying means for piercing and securely engaging the bone, said means for piercing and securely engaging the bone being connected to said means for carrying the suture strand; and means in mechanical cooperation with said carrying means for retaining said means for piercing and securely engaging within the bone, said means for retaining being engagable with said means for piercing and securely engaging the bone, said means for carrying the suture strand being operable to rotate with respect to said means for retaining said means for piercing and securely engaging the bone.

25. The apparatus for securing soft tissues to a bone as set forth in claim 24, wherein said means for piercing and securely engaging the bone includes a generally cone-shaped head portion, and wherein said means for carrying the suture strand includes a stem which extends from said generally cone-shaped head portion.

26. The apparatus for securing soft tissues to a bone as set forth in claim 25, wherein said means for retaining said means for piercing and securely engaging the bone includes a collar member engageable with said generally cone-shaped head portion.

27. The apparatus for securing soft tissues to a bone as set forth in claim 26, wherein said collar member includes a plurality of flanges being operable to engage the bone in a manner to resist removal thereof.

28. The apparatus for securing soft tissues to a bone as set forth in claim 27, wherein said generally cone-shaped head portion is integrally constructed with said stem, and wherein said collar member is constructed separately from said generally cone-shaped head portion and said stem.

29. The apparatus for securing soft tissues to a bone as set forth in claim 28, wherein said means for carrying the suture strand further includes an eyelet formed in said stem.

30. An apparatus for anchoring a suture strand to a bone, said suture strand having a first end, a second end and a midportion disposed between the first and second ends, said apparatus comprising:

means for carrying the suture strand at a position along the midportion of the suture strand; and means for piercing and securely engaging the bone, said means for piercing and securely engaging the bone being connected with said means for carrying the suture strand;

means for retaining said means for piercing and securely engaging within the bone, said means for retaining being removably attachable to said means for piercing and securely engaging the bone;

whereby the suture strand is operable to be secured to the bone and the first and second ends of the suture strand may be manipulated to secure the soft tissues to the bone.

* * * * *